United States Patent [19]

Frisch et al.

[11] Patent Number: 4,720,595
[45] Date of Patent: Jan. 19, 1988

[54] NOVEL AGENTS CONTAINING THE COMPOUND 3-TRIFLUOROMETHYL-4-NITROPHENOL

[75] Inventors: Gerhard Frisch, Wehrheim; Paul Bittner, Kriftel, both of Fed. Rep. of Germany

[73] Assignee: Hoechst Aktiengesellschaft, Frankfurt am Main, Fed. Rep. of Germany

[21] Appl. No.: 921,739

[22] Filed: Oct. 22, 1986

[30] Foreign Application Priority Data

Oct. 24, 1985 [DE] Fed. Rep. of Germany ....... 3537854

[51] Int. Cl.$^4$ .................................................. C07C 79/32
[52] U.S. Cl. ...................................................... 568/709
[58] Field of Search ............................................ 568/709

[56] References Cited

U.S. PATENT DOCUMENTS 3,813,446 5/1974 Jacobs ................................. 568/709
4,596,893 6/1986 Eifert et al. ......................... 568/709

FOREIGN PATENT DOCUMENTS 1068505 11/1959 Fed. Rep. of Germany ...... 568/709

OTHER PUBLICATIONS

Whalley "Jour. Chem. Society, London" (1949), pp. 3016–3020.
Yagupol'skii et al., "Chemical Abstracts" vol. 49 pp. 8866–8867.
Belcher et al., "Chemical Abstracts" vol. 49 p. 9649e (1955).
Agriculture & Food Chem. vol. 7, No. 8 (1959) pp. 529–530.

Primary Examiner—Werren B. Lone
Attorney, Agent, or Firm—Curtis, Morris & Safford

[57] ABSTRACT

Agents which contain a combination product of 30 to 90% by weight of 3-trifluoromethyl-4-nitrophenol, which contains 12 to 20% by weight of water, with 10 to 70% by weight of a basic salt of the alkaline earth series or of the metals Zn(II), Al(III), Fe(II) or Fe(III), where appropriate in the presence of a polyalkylene glycol, are suitable and advantageous for controling lampreys, because they release the active compound in a delayed manner.

10 Claims, No Drawings

NOVEL AGENTS CONTAINING THE COMPOUND 3-TRIFLUOROMETHYL-4-NITROPHENOL

German Patent No. 1,068,505 discloses the use of 3-trifluoro-methyl-4-nitrophenol (I) or of its alkali metal salts or ammonium, alkanolamine or alkylamine salts for controlling animal parasites on fish.

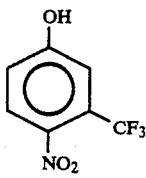 (I)

These parasites include, in particular, the lampreys (*Petromyzon marinus*) from the family of Petromyzontidae. The dose of (I) which is lethal for lamprey larvae is between 2 and 10 ppm, whereas the toxic dose for productive fish or for animals acting as food for productive fish, such as Daphnia, Coleoptera etc., is distinctly higher.

(I) is used during the larval stage of lamprey development, when the efficacy is 90–100%. According to German Patent No. 1,068,505, (I) or its salts is applied in liquid formulations which, in addition to water, contain organic solvents which are miscible with water, such as dimethylformamide, dimethyl sulfoxide, formamide or other solvents of high dipole moment. However, when applied as a liquid formulation incorrect use may result in overdosages which may adversely affect productive fish, especially when multiple application is necessary. Hence it was the object of the present invention to find a new application form which permits more reliable usage of (I) and which has a slow rate of release into bodies of water over a defined period.

It has now been found, surprisingly, that when basic metal salts are added to the compound of the formula I in the presence of a defined amount of water there is formation of solid addition products which are very easy to use, can easily be metered and have, as desired, a slower rate of release of (I).

Hence the present invention relates to agents which contain a combination product composed of 30 to 90% by weight of 3-trifluoromethyl-4-nitrophenol of the formula (I), which contains 12 to 20% by weight, preferably 15 to 18% by weight, of water relative to (I), with 10 to 70% by weight of a basic salt of the metals of the alkaline earth series (Mg(II), Ca(II) and Ba(II)) or of the metals Zn(II), Al(III), Fe(II) or Fe(III).

Particularly suitable basic salts are the oxides, hydroxides, carbonates, bicarbonates, mixed oxyhydroxides or combination salts thereof which contain different metals, such as CaO.MgO, or their hydrates. Of these, the most suitable are the Mg(II) or Ca(II) salts, preferably $Mg(OH)_2$.

When the said basic salts are added to the compound (I), which contains an amount of water as indicated above, there is formation, with a slight increase in temperature, of a salt-like combination product which, on cooling to room temperature, solidifies within 1 to 30 hours. These solids are of very firm consistency. On being placed in water they gradually release the active compound (I) or its metal salt.

The combination product of (I) with basic salts can be obtained in the desired shape, for example in the form of bars, cubes, cylinders etc., so that (I) can be used accurately and safely and its rate of release can be controlled over a lengthy period. Such a so called "slow-release effect" makes it possible better to suit the dosage to the cycle of activity and rest of lamprey larvae. Hence there is no need for multiple additional doses of liquid material.

The formulations preferred in practice are those which contain 70 to 90% by weight of active compound of the formula I (with a water content of 15 to 18% by weight) and 10 to 30% of an abovementioned basic salt.

In another embodiment of the invention, it has been found that the rate of release can be further slowed by addition of polyalkylene glycols, in particular polypropylene glycol (PPG), polyethylene glycol (PEG) or copolymers thereof with a molecular weight between 1,000 and 50,000, to the abovementioned agents; this makes possible a dosage which is even more suitable in practice, and it is possible to suit the dosage to the given conditions even more flexibly. It is possible to add up to 20% by weight, in particular 2 to 12% by weight, of the polymers to the said agents according to the invention.

Examples of polymer types which can be used are the PEG 1500, 4000, 6000, 10000 or 20000 types of HOECHST AG or copolymers of PEG and PPG of the Pluronic ® series of BASF AG.

Furthermore, it is also possible to use synthetic or natural water-soluble waxes in place of the said synthetic polymers.

Moreover, it is also possible to add to the agents according to the invention the wetting and dispersing agents customary in formulations for plant-protection agents. Examples of these are the polyoxyethylated alkylphenol or polyoxyethylated oleylamine or stearylamine and the alkyl- or alkylphenyl-sulfonate types of wetting agent, or dispersing agents, such as sodium lignate, sodium dinaphthylmethanedisulfonate or sodium oleoylmethyltaurate.

For practical use, it is advantageous to dispense the agent according to the invention while it is still liquid into containers which have conical openings at the top and are lined with water-soluble polyvinyl alcohol film bags and are closable, so that once the mixture has solidified it can be removed—without coming into contact with the product—and used. The range of weights for these solids packed in this way is arbitrary; however, it is preferably between 10 and 10,000 g.

The Examples which follow serve to illustrate the invention.

FORMULATION EXAMPLES

Example 1

A cube weighing 10 g and composed of
82% by weight of the compound of the formula I with a water content of about 15% by weight and
18% by weight of $Mg(OH)_2$
was prepared by stirring together the components, pouring the mixture out into a suitable mold, and leaving it to stand for 20 hours.

When this cube was gently stirred in water, 50% had dissolved within 1 h, and it had completely dissolved after about 6 h.

Example 2

A cube weighing 10 g was prepared by mixing the components as described in Example 1 and was composed of 82% by weight of the compound of the formula I (water content: about 15% by weight)
12% by weight of Mg(OH)$_2$ and
6% by weight of PEG 6000.

In water, about 25% of this cube dissolved within 6 h; about 50% had dissolved after 20 h; and it had dissolved after 35 h.

Comparison Example

A cube weighing 10 g and composed of
82% by weight of the compound of the formula I (water content about 15% by weight) and
18% by weight of PEG 6000
was prepared.

The cube released only minimal amounts of the active compound, and these were too small to guarantee adequate control of the lampreys.

We claim:

1. A composition comprising a solid combination product of 30 to 90% by weight of 3-trifluoromethyl-4-nitrophenol of the formula I

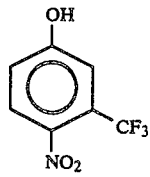

which contains 12 to 20% by weight of water, with 10 to 70% by weight of a basic salt of the alkaline earth series or of the metals Zn(II), Al(III), Fe(II) or Fe(III).

2. A composition as claimed in claim 1, which contains as basic salts oxides, hydroxides, carbonates, bicarbonates, mixed oxyhydroxides or their combination salts with various metals.

3. A composition as claimed in claim 1, which contains 70 to 90% by weight of active compound of the formula I.

4. A composition as claimed in claim 1, which contains Mg(OH)$_2$ as basic salt.

5. A composition as claimed in claim 1, wherein the water content of the compound of the formula I is 15 to 18% by weight.

6. A composition as claimed in claim 1, which contains up to 20% by weight of a polyalkylene glycol.

7. A composition as claimed in claim 6, which contains as polyalkylene glycol polyethylene or polypropylene glycol or their copolymers with a molecular weight of 1,000 to 50,000.

8. A method for controlling lampreys, which comprises treatment of their larvae or their habitat with a composition as claimed in claim 1.

9. A composition as claimed in claim 1, which contains 10 to 30% by weight of the basic salt.

10. A composition as claimed in claim 1, which contains 70 to 90% by weight of active compound of formula I containing 15 to 18% by weight of water and 10 to 30% by weight of the basic salt.

* * * * *